(12) United States Patent
Guldalian

(10) Patent No.: US 9,668,904 B2
(45) Date of Patent: Jun. 6, 2017

(54) SEGMENTED ORTHOSIS WITH A PULLEY MECHANISM FOR FITTING ADJUSTMENT

(71) Applicant: Eric Guldalian, Abington, PA (US)

(72) Inventor: Eric Guldalian, Abington, PA (US)

(73) Assignee: Neurotron Medical Inc., West Trenton, NJ (US)

( * ) Notice: Subject to any disclaimer, the term of this patent is extended or adjusted under 35 U.S.C. 154(b) by 300 days.

(21) Appl. No.: 14/189,829

(22) Filed: Feb. 25, 2014

(65) Prior Publication Data

US 2014/0303536 A1 Oct. 9, 2014

Related U.S. Application Data

(63) Continuation-in-part of application No. 13/775,190, filed on Feb. 24, 2013, now Pat. No. 8,945,033, which is a continuation of application No. 13/460,778, filed on Apr. 30, 212, now Pat. No. 8,382,693.

(60) Provisional application No. 61/480,466, filed on Apr. 29, 2011.

(51) Int. Cl.
*A61F 5/00* (2006.01)
*A61F 5/02* (2006.01)

(52) U.S. Cl.
CPC .................. *A61F 5/028* (2013.01)

(58) Field of Classification Search
CPC ........ A61F 5/028; A61F 5/0193; A61F 5/022; A61F 5/024; A61F 5/30; A43B 13/182; A43B 13/184; A47B 97/00; A47F 7/166; B25J 1/04; B61B 12/02; B61B 7/06; B62H 3/12; B66C 21/02; E04D 13/0765
USPC ........................................ 602/19; 2/336–338
See application file for complete search history.

(56) References Cited

U.S. PATENT DOCUMENTS

| | | | | |
|---|---|---|---|---|
| 5,437,617 A * | 8/1995 | Heinz et al. | ..................... | 602/19 |
| 6,322,529 B1 * | 11/2001 | Chung | ............................. | 602/19 |
| 6,676,620 B2 * | 1/2004 | Schwenn et al. | ............... | 602/12 |
| 7,001,348 B2 * | 2/2006 | Garth et al. | ...................... | 602/5 |

\* cited by examiner

*Primary Examiner* — Michael Brown
(74) *Attorney, Agent, or Firm* — Muskin & Farmer LLC

(57) ABSTRACT

A segmented lumbosacral orthosis with two side members conjoined by a cord threaded through an array of seamless tubes that are independently mounted and swivel from an axis point proximal to the end points of each tube. Each tube array is housed in a mounting bracket made from a continuous piece of material folded over to form a gap in between two sides. Each mounting bracket is attached to a side member by sliding a pin along the folded edge of the bracket through knuckles (or loops) attached to the side member similar to a hinge. A removable posterior member is connected to each posterior end of the side members using an elastic material that expands and contracts in parity with the mechanical advantage closure system. The removable posterior panel is designed to hold a rigid or semi-rigid insert stored in three separate sections: one in a center compartment juxtaposed by one on each side that sway along a vertical axis.

22 Claims, 8 Drawing Sheets

SEGMENTED ORTHOSIS WITH A PULLEY MECHANISM FOR FITTING ADJUSTMENT

CROSS REFERENCE TO RELATED APPLICATIONS

This application is a continuation in part of application Ser. No. 13/775,190 which is a continuation application of application Ser. No. 13/460,778 which claims benefit to provisional application 61/480,466, filed on Apr. 29, 2011, entitled "Segmented Orthosis with a Quasi-Pulley Mechanism for Fitting Adjustment, all three of these applications are incorporated by reference herein in their entireties.

BACKGROUND OF THE INVENTION

The present invention relates to orthosis and, more particularly, to a segmented orthosis with a pulley mechanism for fitting adjustment.

Orthosis braces on the market include a variety of closure systems to conjoin and hold a support member(s) in a desired position once it is wrapped around a location on the body. This type of medical device can be applied around the torso to support the low back, the leg to support a knee, etc. Some of the existing closure systems found on orthosis braces include: (1) belts and/or straps that are pulled and secured using hook and loop fastening methods; (2) threading cord through a series of eyelets; and (3) threading cord around a series of pulleys. The use of cord and pulleys is commonly known as a mechanical advantage system, which can also include substitutes for a pulley, such as a fixed position vertical post or a layering of members to form a channel.

Patients with certain medical conditions may have limited grip strength or range of motion, and therefore have difficulty achieving a recommended compression level when applying an orthosis brace. In these cases, the lack of restrictive movement or bodily support impacts the clinical efficacy while wearing an orthosis. To assist patients with meeting the physical requirements to properly tighten an orthosis brace, a closure system designed with mechanical advantage offers great ease and usability.

Orthosis braces that are currently available on the market with a mechanical advantage closure system have the following deficiencies: (1) they can integrate an array of narrow eyelets that abruptly change a cord's vector to an acute angle thus causing the cord to move unevenly when pulled; (2) they can wrap a cord around a fixed position, straight, vertical post or protrusion off a base, which allows a cord to shift along the length of the vertical axis when drawn; (3) they can have cord lengths that are not easily shortened by a patient to reduce the arm extension distance required to achieve a tight form fit around the treatment area; (4) they can be difficult to center against the treatment area without stopping to shift the orthosis prior to reaching the maximum applied forces; (5) they do not allow the closure system to be easily separated from the connecting support members for routine cleaning, maintenance, repair, and/or replacement; (6) they can have fully exposed elements that protrude outward enough to unexpectedly get caught on an object(s) thus creating a safety hazard; (7) they can integrate a rigid support member with a pre-determined shape and/or contour, which may not conform to every patient's anatomical shape and/or size; (8) they do not include an anterior rigid or semi-rigid insert that can be moved laterally left or right for horizontal realignment; and (9) they can be expensive to produce due to the number and complexity of custom shaped or molded components required for the closure system.

Orthosis devices with strap or belt closure systems can be difficult to tighten around the torso for patients inflicted with certain medical condition(s), such as arthritis, muscle weakness, limited range of motion, etc. As a result of wearing an orthosis with an inadequate or loose fit around a bodily location, the treatment outcome can be less effective for the patient. In addition, supportive rigid or semi-rigid inserts that are not correctly or consistently positioned against a bodily location can have an adverse effect on the treatment outcome.

As can be seen, there is a need for an improved orthosis device that has a mechanical advantage closure system.

DETAILED DESCRIPTION OF THE INVENTION

Figure 1:
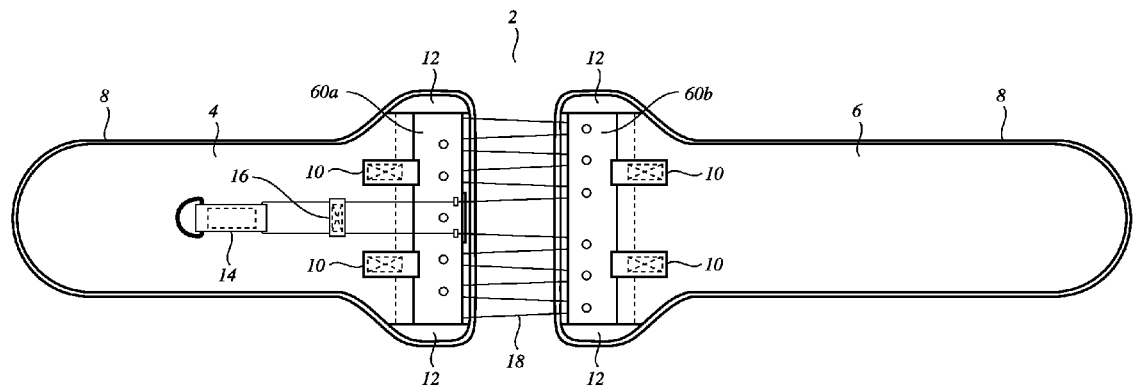
FIG. 1 is an exterior view of an orthosis device, according to an embodiment.
Figure 2:
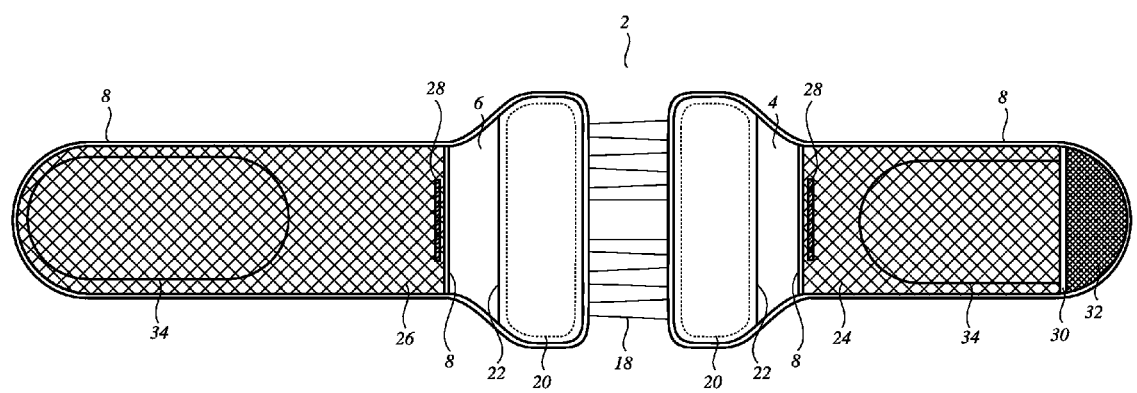
FIG. 2 is an interior view of the orthosis device of FIG. 1, according to an embodiment.
Figure 3:
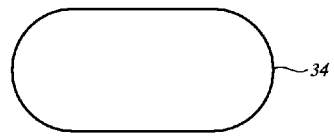
FIG. 3 is a front view of a side member insert that may optionally be used in the orthosis device of FIG. 1, according to an embodiment.
Figure 4:
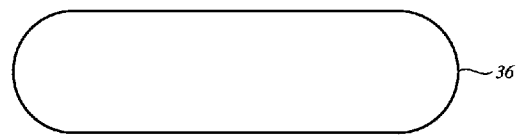
FIG. 4 is a front view of another embodiment of a side member insert that may optionally be used in the orthosis of FIG. 1, according to an embodiment.
Figure 5:
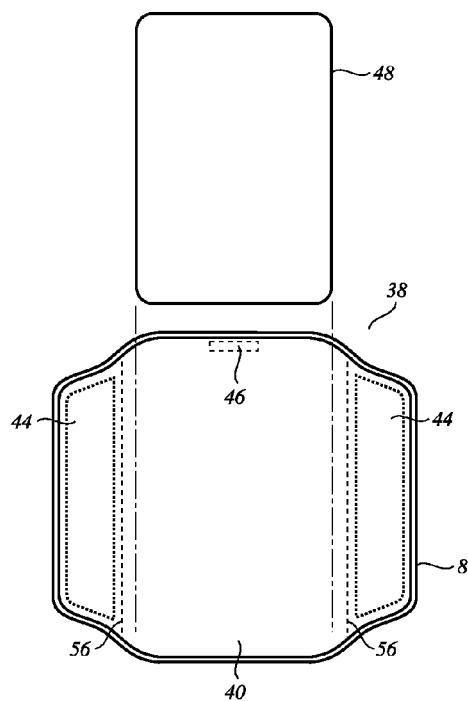
FIG. 5 is an exploded interior view of a removable posterior member used in the orthosis device of FIG. 1, according to an embodiment.
Figure 6:
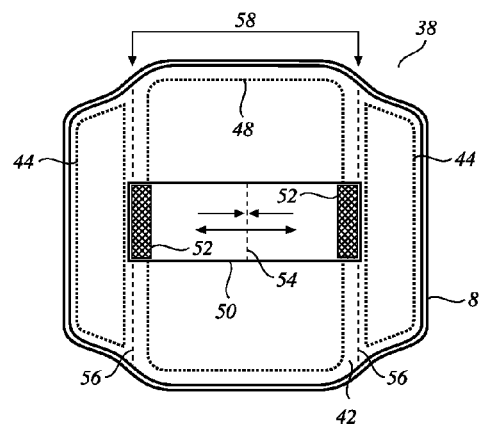
FIG. 6 is an exterior view of the removable posterior member of FIG. 5 with an elastic positioner positioned in a first position, according to an embodiment.
Figure 7:
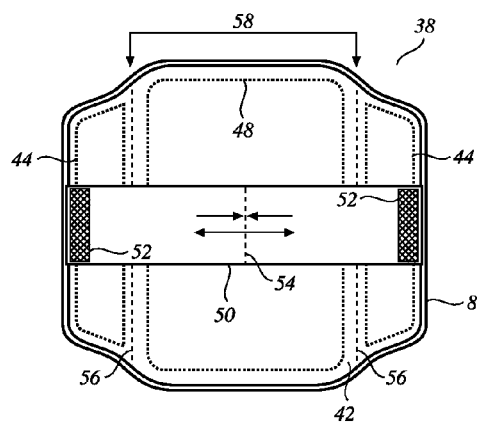
FIG. 7 is an exterior view of the removable posterior member of FIG. 5 with the elastic positioner positioned in a second position, according to an embodiment.
Figure 8:
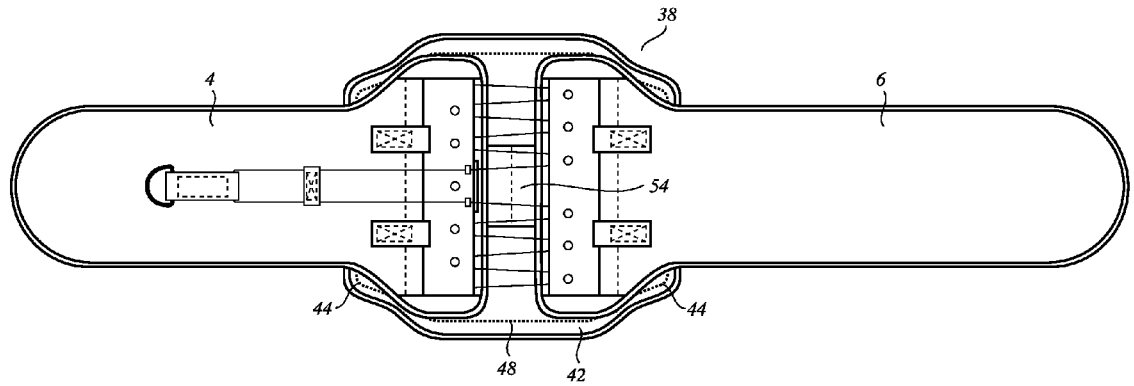
FIG. 8 is exterior view of the orthosis device of FIG. 1 with the removable posterior member of FIG. 5, according to an embodiment.
Figure 9:
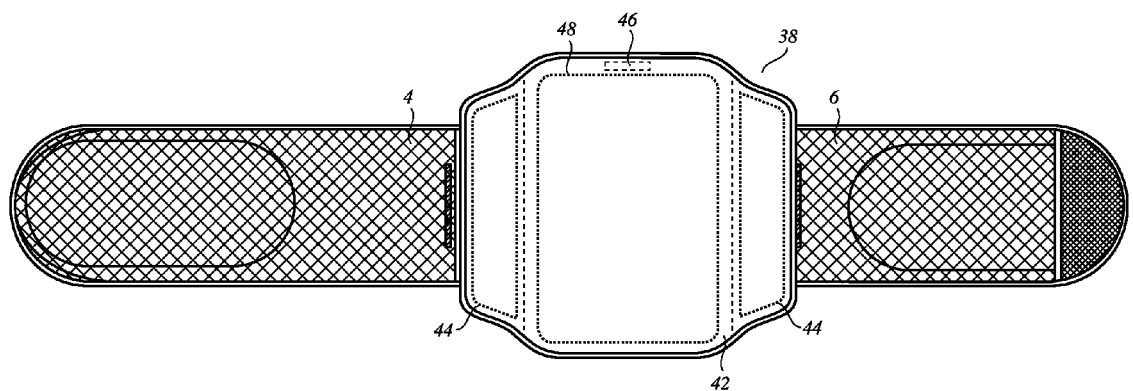
FIG. 9 is an interior view of the orthosis device of FIG. 1 with the removable posterior member of FIG. 5, according to an embodiment.
Figure 10:
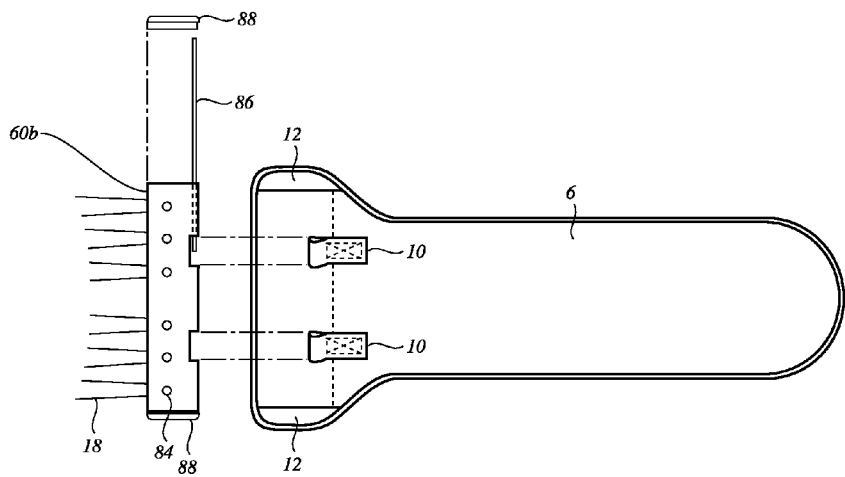
FIG. 10 is a partially exploded view of a portion of the orthosis device of FIG. 8, according to an embodiment.
Figure 11:
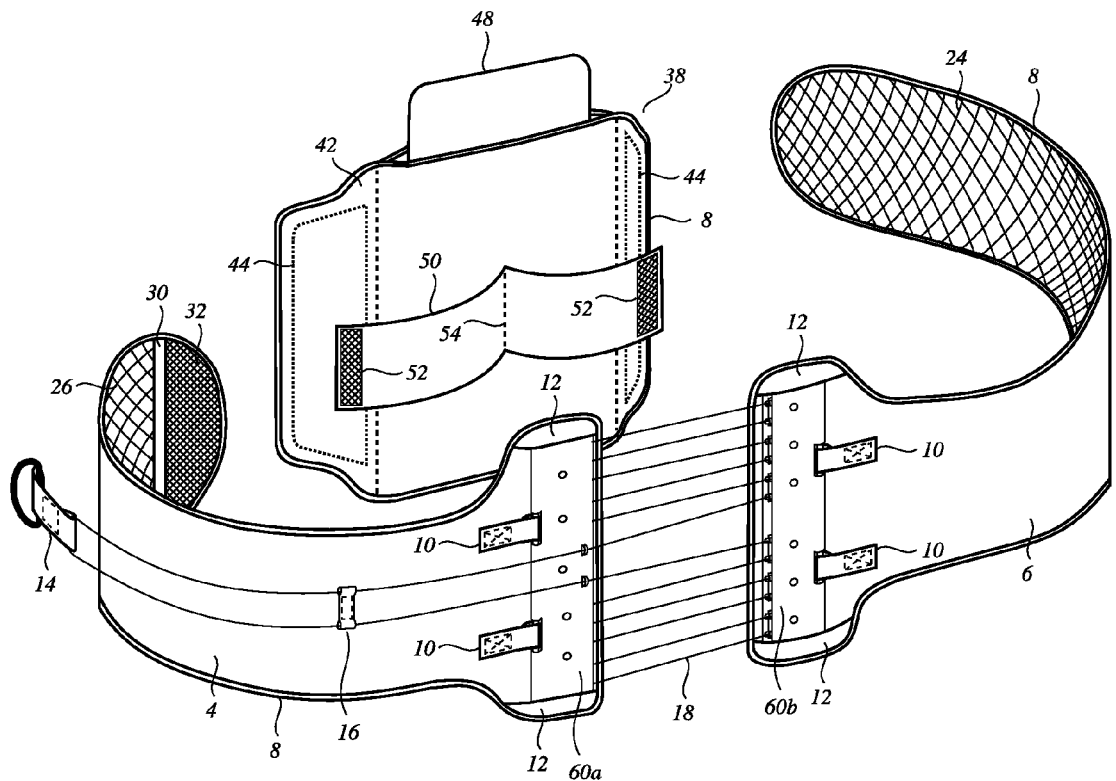
FIG. 11 is a perspective view of the orthosis device of FIG. 8, according to an embodiment.

The following detailed description is of the best currently contemplated modes of carrying out exemplary embodiments of the invention. The description is not to be taken in a limiting sense, but is made merely for the purpose of illustrating the general principles of the invention, since the scope of the invention is best defined by the appended claims.

Various inventive features are described below that can each be used independently of one another or in combination with other features.

An embodiment of the present invention provides a segmented lumbosacral orthosis with mechanical advantage that integrates two side members conjoined by cord threaded through an array of seamless tubes that are independently mounted and swivel from an axis point proximal to the end points of each tube. Each tube array is housed in a mounting bracket made from a continuous piece of material folded over to form a gap in between two sides. Each mounting bracket is attached to a side member by sliding a pin along the folded edge of the bracket through knuckles (or loops) attached to the side member—similar to a hinge. A removable posterior member is connected to each posterior end of the side members using an elastic material that expands and contracts in parity with the mechanical advantage closure system. The removable posterior panel is designed to hold a rigid or semi-rigid insert stored in three separate sections: one in a center compartment juxtaposed by one on each side that sway along a vertical axis. Each side member is capable of storing a removable rigid or semi-rigid insert that can be repositioned along a horizontal axis to provide anterior support.

The pulley (or "quasi-pulley") design is based on a seamless segment of round tubing that is turned to an angle of approximately 180 degrees, and mounted to a rotating carrier. A tube's cross-sectional shape is geometrically round or convex and conforms to the cross-sectional shape of a preferred cord allowing it to slide smoothly and evenly in two directions through a plurality of pulleys.

Referring to FIGS. 1 through 17, a lumbosacral orthosis 2 may integrate a mechanical advantage closure system designed to pull together first and second side members 4, 6. The side members 4, 6 may be wrapped around the torso of a user for an anatomically contoured fit. The side members 4, 6 may be made of a flexible base material, such as fabric, foam, or the like, which has an exposed pile on one or both sides forming loops for compatibility with hook fasteners.

Hook fasteners are a connection mechanism that can be used to connect two surfaces together, such as VELCRO (which uses a first surface comprising hooks and a second surface comprising loops which cooperate to stick together). The outer shape of the side members 4, 6 may be comprised of both rectilinear and curvilinear lines. The side members 4, 6 may be capable of storing a rigid or semi-rigid material as an anterior support. The first side member 4 may connect to second side member 6 through a posterior pulley system and an anterior fastener 32. The anterior fastener 32 may be a hook fastener used to close the anterior portion of the orthosis 2 by attaching the interior side of the first side member 4 to the exterior side of the second side member 6. The hook fastener may be sewn into the first side member 4 and may attach to the loop pile of the second side member 6.

Binding 8 may be a fabric material sewn along exposed edges of the side members 4, 6 to provide reinforcement and an aesthetically pleasing appearance. The binding 8 can be made of, for example, cotton, polyester, polyester-cotton blend, nylon, and the like.

Anterior support may be provided by rigid or semi-rigid inserts 34, 36 that can be added or removed from compartments 24, 26 within the orthosis 2. The inserts 34, 36, once inserted into the compartment 24, 26 of the side members 4, 6, may provide anterior support when the device is wrapped firmly against the torso. The anterior insert can slide along the length of the compartment's interior for optimal clinical efficacy. When the anterior inserts 34, 36 are within both side members 4, 6 and the side members 4, 6 are overlapped, the rigidity and support may increase. Alternatively, a clinician can reduce the amount of anterior support by removing one or both rigid inserts 34, 36. The inserts 34, 36 may be made from, for example, plastic, such as polyethylene, polypropylene, or acrylonitrile-butadiene-styrene (ABS). The outer shape of the inserts 34, 36 may include both rectilinear and curvilinear lines.

The compartments 24, 26 may optionally hold other items, such as a hot pack, a cold pack or the like. The item in the compartments 24, 26 may be horizontally shifted left to right within the compartments 24, 26 to adjust the placement for optimal clinical efficacy. The compartments 24, 26 may be made of, for example, a 3-D spacer mesh that is sewn to the side members 4, 6. A hook fastener 28 for the compartments 24, 26 may be attached to the inside of the compartments 24, 26 to seal and unseal an open end of the compartments 24, 26. The hook fastener 28 can attach to the loop pile side of the side members 4, 6. A ribbon 30 may be used for aesthetic purposes to cover the stitched edge that joins the 3-D spacer mesh to the hook fastener 28 on the first side member 4. The ribbon 30 can be made from, for example, polyester, nylon, or a combination thereof.

A side member posterior insert 20 may provide posterior support when the orthosis 2 is wrapped firmly against the torso of a user. The insert 20 may be made from plastic, such as polyethylene or polypropylene. The outer shape of the insert 20 may include both rectilinear and curvilinear lines. A cover 22 for the insert 20 may be overlaid on top of the insert 20 and permanently stitched to a side member 4, 6. The cover 22 may be made from a flexible base material, such as fabric, foam, or the like, which has an exposed pile on one or both sides, forming loops for compatibility with hook fasteners. The outer shape of the cover 22 may include both rectilinear and curvilinear lines.

A posterior support member 38 may store a centralized rigid or semi-rigid insert 48, along with two juxtaposed supports 44 that may sway to varying degrees, all of which rest against the lumbosacral area for an anatomically contoured fit. The support member 38 may attach and detach from interior ends of the side members 4, 6. A center compartment 58 of the posterior support member 38 may be formed between an interior panel 40 and an exterior panel 42 of the support member 38. The panels 40, 42 may each have loop properties on both sides thereof. A hook fastener 46 may be disposed near the opening of the center compartment 58, between the panels 40, 42, to open and close the compartment 58. The central compartment 58 may store accessories, such as a rigid or semi-rigid insert 48, a hot pack, a cold pack or the like. The removable posterior panel 38 may be attached to the first and second side members 4, 6 that attaches to hook fasteners 52 which are affixed to a segment of elastic 50 that expands and contracts. First and second side members 4,6 comprise loop fasteners or material with loop properties to attach to the hook fasteners 52. This method of fastening the removable posterior panel 38 may provide quick attachment to and detachment from the orthosis 2, and may allow the center point of the removable posterior panel 38 to be adjusted both horizontally and vertically.

Once inserted into the compartment 58 of the posterior member 38, the insert 48 may provide posterior support against the lumbosacral area when the device is wrapped firmly against the torso. The insert 48 may be made of, for example, flexible plastic, such as polyethylene or polypropylene. Alternatively, the insert 48 may be made from a rigid material plastic, such as acrylonitrile-butadiene-styrene (ABS). The outer shape of the insert 48 may include both rectilinear and curvilinear lines. In some embodiments, the insert 48 may be formed as a frame-shaped member, similar to the insert 48 of FIG. 5, except a central section of material removed. This configuration may provide less pressure on a user's spine, for example, while still providing lateral support. In other embodiments, the compartment may be formed as two compartments formed on each side of the compartment 58. This may be accomplished, for example, by sewing a seam on each side of the compartment. In each of these compartments, an insert may be disposed. In this configuration, no part of the insert may cross over the user's spine.

An elastic positioner 50 may be used to set the horizontal and vertical alignment of the posterior member 38 against the posterior sections of the side members 4, 6. The elastic property of the positioner 50 allows it to expand and contract in parity with the interstitial space formed between the side members 4, 6 once it is attached to each respective end. Hook fasteners 52 may be used to attach both ends of the elastic positioner 50 to the respective ends of each side member 4, 6. When the brackets 60*a* 60*b* are pulled closer together (or farther apart) the elastic positioner 50 can adjust in size (by virtue of it being elastic) to cooperate with the change in distance between the brackets 60*a* 60*b* thus maintain the connection of the support member 38 to the side members 4, 6. While one elastic positioner 50 is shown in the figures, any appropriate number of elastic positioners 50 could be used. For example, two or more elastic positioners 50 may be positioned at the posterior member 38.

A center attachment point 54 may include a stitch, or an alternative fastener method, adapted to secure the elastic positioner's midpoint against the exterior panel 42 of the posterior member 38. In alternate embodiments, the elastic positioner 50 may be formed using two or more pieces, spaced apart from one another, with each piece secured against the exterior panel 42 of the posterior member 38. A sway line 56 may be a vertical stitch that helps encapsulate the lateral rigid or semi-rigid inserts 44 while, at the same time, forms the sides of the center compartment 58. In addition, it allows the posterior panel to become concave in shape and thus conform to the natural contour of a patient's lumbosacral area.

As the orthosis 2 is cinched around the torso, the first and second side members 4, 6 may glide over the exterior side of the removable panel 38 encapsulating lateral supports 44. The supports 44 may be placed between the interior and exterior panels 40, 42 of the removable posterior member 38. The supports 44 may be made from a flexible plastic, such as polyethylene or polypropylene. The outer shape of the supports 44 may include both rectilinear and curvilinear lines.

The mechanical advantage closure system may be operated by a pull member 14 attached to a cord 18 that loops through a series of opposing pulley assemblies 74 to expand or contract the interstitial space between the first and second side members 4, 6. The cord 18 may be made from a braided aramid fiber, such as KEVLAR. Alternatively, the cord 18 could be made from a braided carbon fiber. In other embodiments, the cord 18 could be made from braided natural or synthetic fibers, such as nylon, polyester, or a combination thereof. The pulley assembly 74 may be based on a seamless segment of round tubing 78 bent approximately 180 degrees from one end to the other. The tube's 78 lack of seams and convex shape allow a cord 18 to slide evenly and with reduced friction. In addition, by placing the tube 78 in a carrier 76 that rotates, the pulley assembly 74 can pivot left and right along a plane as the cord changes its path.

A sliding cord guide 16 may be designed to feed cord through open loops at each end and limit the vertical movement of the cord once the device is secured around the torso. The sliding cord guide 16 may have a hook fastener on one side that may attach and detach to a point anywhere along the side member 4.

Since the mechanical system closure system is not permanently fastened to the first or second side member 4, 6, it can be detached and re-attached for maintenance or repair purposes without rendering the entire orthosis 2 useless. For example, pulley mounting brackets 60*a*, 60*b* may be removed by removing an end cap 88 and a pin 86 from the brackets 60*a*, 60*b*. A pin round-over 62 may help hold the pin 86 in place. The pin 86 may pass through at least one flexible knuckle 10 that may be attached to each side member 4, 6. The flexible knuckle 10 may be a flexible material, such as webbing, formed into an open loop at one end, through which the pin 86 may pass through. A slot 12 may be formed in the side members 4, 6 for holding the ends of the brackets 60*a*, 60*b*.

First and second pulley mounting brackets 60*a*, 60*b* may be made from a continuous piece of material, such as metal or plastic, that is folded over to form a gap between the newly formed top and bottom portions. The brackets 60*a*, 60*b* could have straight, beveled, and/or round corners. Each bracket may be used to mount pulley assemblies 74 using fasteners 84. A fully assembled bracket, such as bracket 60*a*, may be attached to a side member, such as side member 4. The brackets 60*a*, 60*b* could be made from metal or plastic. Each bracket 60*a*, 60*b* may be made in any appropriate length and may include any number of pulley assemblies 74. While FIG. 12, for example, shows 5 pulley assemblies 74 on one bracket 60*a* and 6 pulley assemblies 74 on bracket 60*b*, any number of pulley assemblies 74 may be used in each bracket 60*a*, 60*b*. Typically, one bracket may include one additional pulley assembly as compared to its corresponding bracket. The size of each bracket 60*a*, 60*b* and the number of pulley assemblies 74 in each bracket may depend, for example, on the height and intended use of the orthosis.

First mounting bracket pulley fastener apertures 64*a*, 64*b* may be pre-punched or pre-drilled holes aligned in pairs that may be used to slide through a bushing 80 and round fastener 84 for the pulley assembly 74. The bushing 80 and round fastener 84 could be made of, for example, metal, such as steel, bronze, and the like; or plastic, such as acetal, nylon, polypropylene, and the like. A mounting bracket pocket 66 may be a notch formed in the mounting bracket that receives the flexible knuckle 10 affixed to a side member 4, 6—similar to a hinge. A cord tie-down aperture 68 may be a pre-punched or pre-drilled hole that may be used to connect a cord end to a mounting bracket 60*a*, 60*b*. A cord eyelet aperture 70 may be a pre-punched or pre-drilled hole that allows an eyelet to be passed through a mounting bracket to the top outer surface or plane. Second mounting bracket pulley fastener apertures 72*a*, 72*b* may be pre-punched or pre-drilled holes aligned in pairs that are used to slide through a bushing 80 and round fastener 84 for the pulley assembly 74. The bushing 80 and round fastener 84 could be made of, for example, metal, such as steel, bronze, and the like; or plastic, such as acetal, nylon, polypropylene, and the like.

The pulley assembly 74 may be a seamless segment of round tubing 78 shaped to an approximately 180 degree angle that may later be inserted into a carrier 76 with two holes aligned to the open ends of the tube 78. The tube's 78 geometric shape may limit the insertion depth through the carrier holes 76. A bushing 80 may be inserted into the tube carrier 76 to hold the back end of the tube 78 in place thus limiting or preventing forward or backward movement. The seamless tube carrier 76 may be a continuous piece of material with a three dimensional shape that includes two sets of holes: one is aligned for the two ends of the seamless tube 78; and another for the bushing 80. The carrier may serve two main purposes: (A) to hold a seamless tube in place; and (B) to connect the pulley assembly to a mounting bracket. The seamless tube carrier 76 may have straight or round exterior corners and could be made from a metal, such as aluminum, steel, brass, and the like; or a plastic, such as nylon, ABS, and the like. When made from plastic, the interior corners may include a fillet for structural reinforcement. The outer shape could be rectilinear, curvilinear, or a combination thereof. The seamless tube 78 may be a segment of round tubing material made from either a metal, such as aluminum, steel, brass, or the like; or a plastic, such as nylon, ABS, or the like. The bushing 80 may be a cylindrical material consisting of an open core that could be made from either a metal, such as aluminum, steel, brass, bronze, or the like; or a plastic, such as nylon, ABS, or the like. The bushing 80 may allow the tube carrier 76 to rotate left and right once attached to a mounting bracket 60*a*, 60*b* using a round fastener 84 with an outer diameter smaller than the inner diameter of the bushing 80.

A cord eyelet block 82 may be used to direct the cord as it is pulled across a mounting bracket. Its design includes both exposed and unexposed portions. The exposed portions may be shaped as eyelets protruding upward through the mounting bracket, and a half round protruding outward from the side of the bracket to prevent the cord from rubbing on a straight edge. The unexposed portion may rest inside the first mounting bracket aligned to apertures for receiving a round fastener 84. The round fastener 84 may be used to attach the pulley assembly 74 and cord eyelet block 82 to a mounting bracket. The fastener 84 could be a metal semi-tubular rivet that passes through the apertures in a mounting bracket, bushing, and tube carrier. Alternatively, the fastener 84 could be a two part interlocking male/female rivet design made of either a metal or plastic.

The orthosis 2 of the present invention may include three main support members, and a pulley system for mechanical advantage, which may work in tandem with one another to form a lumbosacral orthosis. Two side support members, which wrap around the left and right side of a torso, may be conjoined by a posterior pulley system affixed to the side members by removable pins. A center posterior support member is affixed to each of the side members using hook fasteners, making its position adjustable and use optional. The first and second side support members and removable posterior support member are made from non-elastic material that will restrict or limit its stretchability while being applied or in use.

To provide the necessary bodily support and/or restrictive movement, the anterior rigid or semi-rigid inserts should be placed in the side member compartments, and the posterior rigid or semi-rigid insert should be placed in the center member compartment. In both cases, the compartments can be sealed by a hook fastener that affixes to the side member material with loop properties.

The circumference of the orthosis is adjusted by a hook fastener and pulling a cord that loops through an array of pulleys, consisting of seamless tubes mounted to a bracket attached to opposing ends of the side members. An initial fit is achieved by wrapping the orthosis around the torso and affixing the two anterior ends of the side members together. A more restrictive fit is achieved by the pulley system that is designed to reduce the distance between the two posterior ends of the side members.

To use the orthosis 2, a gap may be set between the first and second side members by releasing the cord tension through the pulley system—this gap may be reduced during a later step. The rigid or semi-rigid inserts should be placed in the side member compartments and the removable posterior compartment. Without these inserts, limited support will be provided while wearing the orthosis. The compartments on each side member are formed in part using a 3-D spacer mesh that may provide three key benefits: (1) air exchange or movement from one surface to another; (2) visibility to see the position of an insert; and (3) a padding effect that enhances overall comfort. The side member compartments may be designed to allow accessories, such as rigid or semi-rigid inserts, to be moved horizontally left or right so they are aligned over the optimal anatomical location. Furthermore, the quantity or density of all removable inserts can be adjusted as needed by a practitioner.

The orthosis may be positioned around the torso of the user until the removable posterior panel is centered to the lumbosacral area. The end of each side member may be pulled forward until it is tight against the body, and then, may be connected together by affixing the hook fastener on the first side member to the exterior side of the second side member. This initial closure method may be made possible by the hook fastener being compatible with the second side member's loop property. A more restrictive fit may still be necessary.

To make the final fitting adjustment, principles of physics have been applied to reduce the amount of force that is necessary to pull the side members closer to one another using pulleys and cord. The invention has replaced a conventional grooved or convex pulley with a pulley comprised of a seamless round tube, shaped like an arc with an approximately 180 degree angle from open end to open end. The pulley may connect to a carrier designed to pivot from a point proximal to the cord.

While the seamless tube is one unique component to the pulley system, the method of connecting it to the apparatus may be equally important. The connection may be accomplished by inserting the open ends of the seamless tube into a carrier that may swivel around a pivot point. Since the seamless tube is arced to approximately 180 degrees, it may have a limited insertion distance into the carrier. Furthermore, the seamless tube may be held in position by a bushing adjacent to the tube's back end—proximal to the open ends. The pulley assembly's structural design may limit the tube's movement backwards or forwards thereby providing stability during use and operation. The bushing may have an outer diameter slightly larger than the mounting bracket apertures to which it is aligned, an inner diameter slightly larger than an outer diameter of the round fastener, and it is slightly taller than the tube carrier. These properties of the bushing may result in two key benefits: (1) it limits how much the top and bottom of the mounting bracket can be pulled together when a round fastener is attached; and (2) it allows the tube carrier to swivel freely once a round fastener has been attached between the top and bottom sides of a mounting bracket.

The seamless tubes can be made from metal, such as aluminum, brass, or steel that has burrs removed and edges smoothed by sanding or filing. Alternatively, the seamless tube could also be made from plastic, such as nylon, acrylonitrile-butadiene-styrene (ABS), or polypropylene. In addition, a seamless plastic tube could be reinforced by integrating other materials, such as fiberglass. Similarly, the tube carrier can be made from metal, such as aluminum, brass, or steel that has burrs removed and edges smoothed by sanding or filing. Alternatively, the tube carrier could also be made from plastic, such as nylon, acrylonitrile-butadiene-styrene (ABS), or polypropylene. In addition, a tube carrier could be reinforced by integrating other materials, such as fiberglass.

The advantages of using plastic to fabricate the pulley assembly would be smooth and even cord movement, lightweight, and low production cost. Use of a particular metal(s) could be heavier and/or more durable than plastic.

The cord itself may be made from an aramid fiber, commonly known as KEVLAR, which may be braided into a diameter smaller than the diameter of the seamless tubes. The cross sectional shape of the cord may be round, but it could also be braided to other geometrical shapes, such as a square. Alternatively, the braided aramid fiber could be used to make a monofilament with a diameter smaller than the diameter of the seamless tubes. As described above, the cord may be made of any suitable cord material, such as braided natural or synthetic fibers, such as nylon, polyester, a combination thereof, etc. The carriers 76 can be made of any suitable material, such as any metal (e.g., aluminum, etc.) plastic, etc. The tubes can also be made of any suitable material, such as rubber, plastic, etc.

Friction can wear down the fibers in a cord thus resulting in its failure. To minimize cord friction and possible wearing, an insert may be designed with a round edge protruding outward that is flush with the exposed edges of a mounting bracket and perpendicular to the cord.

Engaging the mechanical advantage system may be done by grabbing hold of the pull member and drawing the cord outward away from the body. As the cord is drawn, it may move through the pulleys, fastened to the side members through mounting brackets, and reduce the interstitial space between both side members. The mechanical advantage system may have an upper and lower set of pulleys that may be managed using a continuous piece of cord threaded through two apertures to the underside of the first mounting bracket and knotted at each end. An eyelet block on the first mounting bracket, along with the repositionable cord guide, may limit the possibility of the cord becoming tangled or twisted; and reduces wearing of the cord as it is drawn across the edge of the first mounting bracket.

The output force created by drawing the cord through the pulleys may occur with even and smooth movement. To reduce drag, the pulleys may swivel to change direction with the cord as it is pulled in a zigzag pattern. As the gap between both side members decreases a more restrictive fit can be achieved. Once the side members have made contact with each other the upper limit of applied input force has been reached. To maintain the current cord state, the pull member should be pulled across the anterior portion of the orthosis and firmly engaged to a side member.

To remove the orthosis, the user may disengage the pull member from the side member and move it along with the cord away from the anterior closure section. Next, the user may disengage the hook fastener for the anterior closure of both side members and then fully remove the orthosis from the torso.

To make the invention work even better, the following elements could be added: (1) both open ends of the seamless tube could be flared outward to reduce or minimize cord friction as it moves in either direction. (2) Include two sets of protrusions on the underside of the first mounting bracket that are in close proximity to each cord tie-down aperture for the purpose of winding or coiling unwanted cord length. Since aramid fibers can be very strong and difficult to cut, it would be helpful to provide a simple method of shorting the cord length without requiring any tools. (3) Apertures could be added to the underside of the mounting brackets, which would receive removable pins to enable and disable the swivel aspect of the pulley assemblies. This could be beneficial during production of the invention because mounted pulleys would not move while threading the cord. (4) Include a method to place a marker that can be easily repositioned to align with the anterior center point of a patient's waistline. This will assist a patient with centering the removable posterior member, which is important for proper and consistent use, as well as treatment outcome. The marker could be a continuous band made from a flexible material, such as webbing, that slides along the second side member and is held in position using a hook fastener on one or both sides. Alternatively, the marker could be a segment that attaches to either side of the second side member; or it could be a clip the attaches to the edge(s) of the second side member. Color, labels with text and/or graphics, or a combination thereof could be used to identify the marker and its purpose.

Production could be Compartmentalized into the Following Procedures:

Fabricate Rigid or Semi-Rigid Inserts:

1. Die cut all removable and non-removable pieces of rigid or semi-rigid inserts.

Fabricate Pulley System:

1. Assemble a pull member by sewing a piece of flexible material around a D-ring. Form a cord loop at the opposite end of the flexible material and hold it together until permanently sewn with a reinforced stitch. Sew a piece of hook fastener to one side of the pull member that is positioned between the D-ring and open loop.

2. Die cut or injection mold a set of mounting brackets complete with pre-punched or pre-drilled holes.

3. Place the cord aperture guide in the corresponding mounting bracket and push the eyelets up through the top side of the mounting bracket.

4. Fasten a rivet to secure the cord aperture guide to the mounting bracket.

5. Insert a segment of tubing arced to approximated 180 degree into the gap of a pulley carrier. Push the tube forward through the two corresponding apertures in the pulley carrier until it does not move any further.

6. Place a bushing through the apertures on the pulley carrier.

7. Insert the pulley assembly into the mounting bracket and align the apertures.

8. Install a round fastener (rivet) to the secure the pulley assembly to the mounting bracket.

9. Repeat step 5-8 until all required pulley assemblies have been attached to the mounting brackets.

10. Cut a segment of cord to required length.

11. Feed one end of the cord through the upper cord tie-down aperture and secure with a double knot on the underside of the mounting bracket.

12. Loop the unknotted cord end in a zigzag pattern by alternating it through the seamless tubes on the upper portion of the first and second mounting brackets.

13. Feed the unknotted cord end through the upper cord eyelet on the mounting bracket.

14. Feed the unknotted cord end through the upper loop on the sliding cord guide.

15. Feed the unknotted cord end through the cord loop on the pull member.

16. Feed the unknotted cord end through the lower loop on the sliding cord guide.

17. Feed the unknotted cord end through the lower cord eyelet on the mounting bracket.

18. Loop the unknotted cord end in a zigzag pattern by alternating it through the seamless tubes on the remaining lower portion of the first and second mounting brackets.

19. Feed one end of the cord through the lower cord tie-down aperture and secure with a double knot on the underside of the mounting bracket.

Fabricate First and Second Side Members:

1. Cut the base material with loop properties on both sides to the desired shapes and sizes.

2. Cut the 3-D spacer mesh to the desired shapes and sizes. Cut segments of hook fasteners and sew towards straight end of each piece of spacer mesh. Sew binding material along straight edge of both pieces.

3. Cut hook fastener for attaching side members to the desired shape and size. Align the straight edge of the hook fastener to the corresponding piece of spacer mesh, and sew together with a stitch. Cover the seam with a piece of ribbon cut to the desired length.

4. Cut the covers for the posterior supports to the desired shape and size.

5. On the exterior side of the first side member, position and sew three sides of the cover material cut in step 4. Slide a rigid or semi-rigid insert into the pocket through the remaining open end. Close the open end with a sewing stitch.

6. Form a flexible knuckle (or open loop at one end) using flexible material and hold it together until permanently sewn onto the first side member with a reinforced stitch. Form a second flexible knuckle (or open loop at one end) using flexible material and hold it together until permanently sewn onto the first side member with a reinforced stitch.

7. Cut segments of flexible material to form slots used to tuck in the ends of mounting bracket, and sew them to the first side member.

8. On the interior side of the first side member, position and sew the outer edges of the spacer mesh with the hook fastener to the base material.

9. Sew binding material around entire outer edge of first side member.

10. On the exterior side of the second side member, position and sew three sides of the cover material cut in step 4. Slide a rigid or semi-rigid insert into the pocket through the open end. Close the open end with a sewing stitch.

11. Form a flexible knuckle (or open loop at one end) using flexible material and hold it together until permanently sewn onto the second side member with a reinforced stitch. Form a second flexible knuckle (or open loop at one end) using flexible material and hold it together until permanently sewn onto the second side member with a reinforced stitch.

12. Cut segments of flexible material to form slots used to tuck in the ends of mounting bracket, and sew them to the first side member.

13. On the interior side of the second side member, position and sew the outer edges of the spacer mesh to the base material.

14. Sew binding material around entire outer edge of second side member.

Fabricate Removable Posterior Panel:

1. Cut the interior and exterior pieces using material with loop properties on both sides to the desired shapes and sizes.

2. Cut segment of hook fastener and sew on upper end of interior piece.

3. Sew binding material along straight edge of interior piece that will form open end of compartment.

4. Cut a segment of elastic.

5. Cut two segments of hook fastener and permanently sew them to each end of the elastic segment.

6. Position the segment of elastic to the horizontal and vertical center point of the exterior piece, facing outward, and permanently affix it with a reinforced sewing stitch.

7. Overlay both the interior and exterior pieces and sew vertical stitches to form sway line for lateral supports.

8. Slide a lateral rigid or semi-rigid insert between each open end of the interior and exterior pieces.

9. Sew binding material around entire outer edge of both the interior and exterior pieces.

10. Slide rigid or semi-rigid insert into the center compartment. Seal the open end with the hook fastener.

Final Assembly:

1. Align and place the two flexible knuckles on the first side member within the pockets on the first mounting bracket. Slide a pin through the back side of the mounting bracket.

2. Bend each pin round-over to keep the pin snug against the back end of the mounting bracket.

3. Insert end caps into the first mounting bracket.

4. Tuck each end of the first mounting bracket into the corresponding slot on first side member.

5. Align and place the two flexible knuckles on the second side member within the pockets on the second mounting bracket. Slide a pin through the back side of the first mounting bracket.

6. Bend each pin round-over to keep the pin snug against the back end of the second mounting bracket.

7. Insert end caps into the second mounting bracket.

8. Tuck each end of the second mounting bracket into the corresponding slot on second side member.

9. Affix pull member to the exterior side of first side member.

10. Slide rigid or semi-rigid insert into the interior compartment on first side member. Seal the open end with the hook fastener.

11. Slide rigid or semi-rigid insert into the interior compartment on second side member. Seal the open end with the hook fastener.

12. Place the first and second side members on a flat surface with the interior side facing up. Affix removable posterior member to the first and second side members using the hook fasteners on the elastic positioner.

Figure 12:
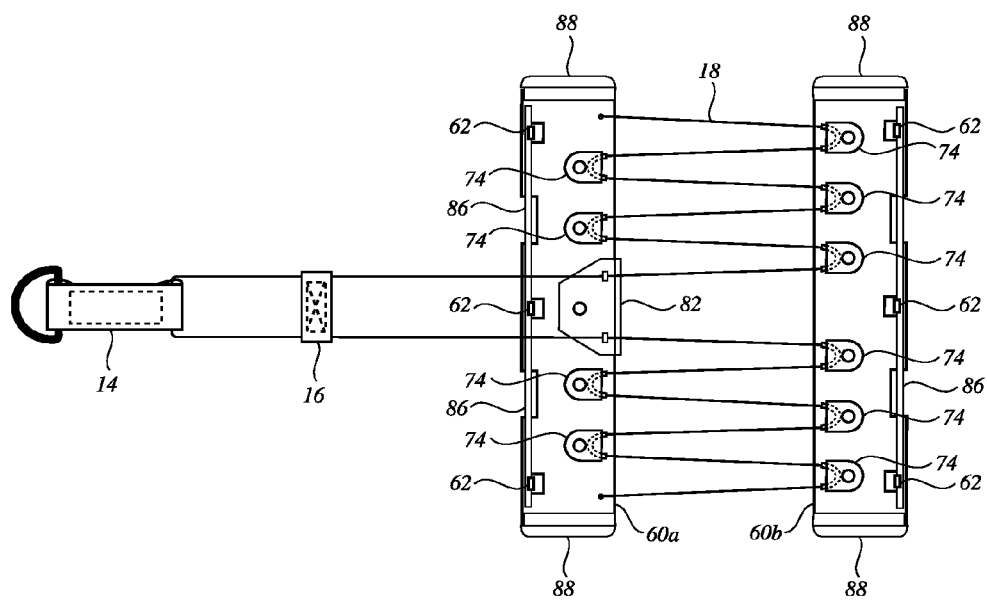
FIG. 12 is a front view of a mechanical advantage closure system used in the orthosis device of FIG. 1, according to an embodiment.
Figure 13:
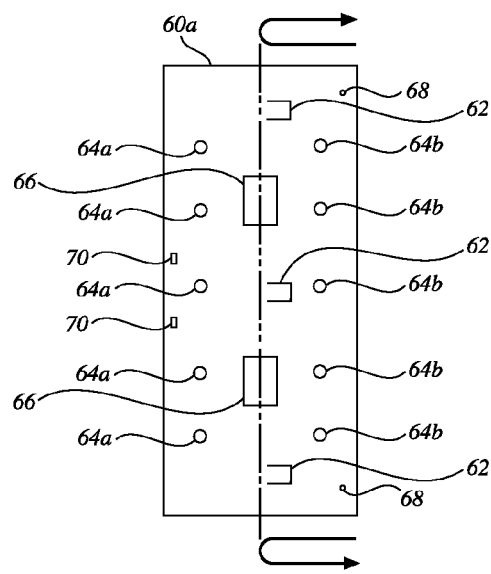
FIG. 13 is front view of a pulley mounting bracket used in the mechanical advantage closure system of FIG. 12, according to an embodiment.
Figure 14:
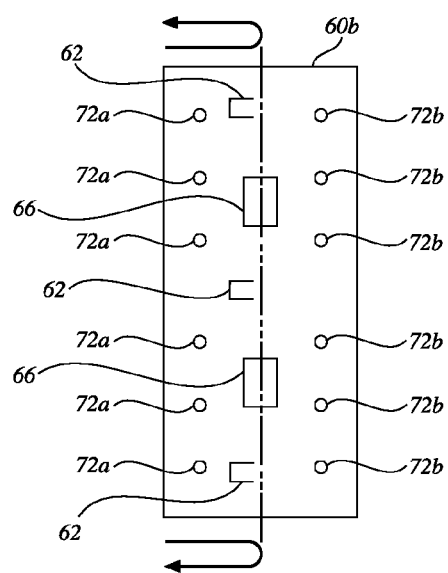
FIG. 14 is a front view of another pulley mounting bracket used in the mechanical advantage closure system of FIG. 12, according to an embodiment.
Figure 15:
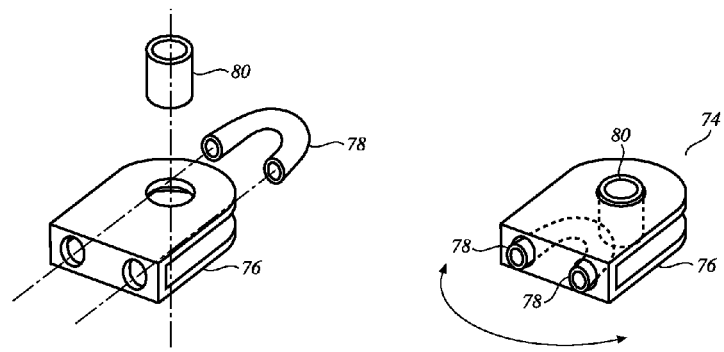
FIG. 15 includes an exploded and a perspective view of a pulley assembly used in the mechanical advantage closure system of FIG. 12, according to an embodiment.
Figure 16:
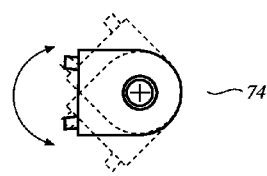
FIG. 16 is a top view of the pulley system of FIG. 15, according to an embodiment.
Figure 20:
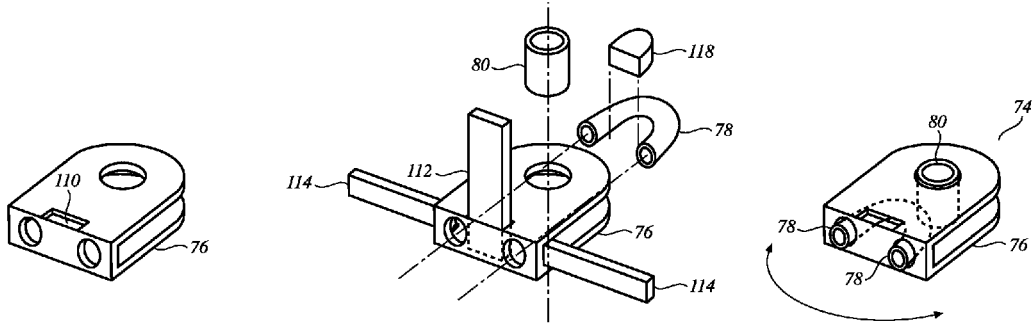
FIG. 20 is a drawing of a pulley assembly used in the mechanical advantage closure system of FIG. 12 with an opening in the carrier, according to an embodiment.
Figure 21:
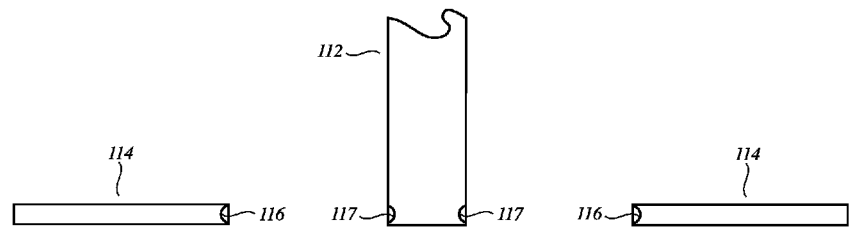
FIG. 21 is a drawing of an inner alignment tool and outer alignment tools used to assist insertion of a respective tube, according to an embodiment.

FIG. 20 is a drawing of a pulley assembly used in the mechanical advantage closure system of FIG. 12 with an opening in the carrier, according to an embodiment. FIG. 21 is a drawing of an inner alignment tool and outer alignment tools used to assist insertion of a respective tube, according to an embodiment.

To assist with the process of assembling the quasi-pulleys 74 a new cutout or opening 110 can be formed on the top side of a carrier 76 to receive a custom fabricated inner alignment tool 112. The opening 110 does not pass completely through a bottom of the carrier so that the tool 112 can fit securely inside the carrier 76. The inner alignment tool 112 is used to help adjust the angle of a tube segment to achieve proper alignment. The opening 110 would span the distance between the interior edges of the small holes, or beyond those two initial reference points. Alternatively, a single opening 110 could be replaced with two or more smaller openings that equally allow a plurality of custom tooling to be inserted for hole/channel alignment purposes. In addition to the inner alignment tool 112, outer alignment tools 114 could be temporarily inserted through the already open sides of a carrier 76 to form a set of restraints around each small hole. Both the inner alignment tool 112 and outer alignment tool 114 can have concave notches 116, 117 and/or other semi-circle attributes that are designed to gradually move the open ends of a tube towards the center point of each respective hole as it is being inserted. Once the tube is properly inserted and the proper adjustments made, the custom alignment tools 112, 114 would then be removed and the opening 110 would serve no other purpose. The custom alignment tools 112, 114 could be oriented in and out of position via a hand held operation; integrating them into a mechanized machine; or a combination thereof. The custom alignment tools 112, 114 are optional and embodiments can be made with only the inner alignment tool 112, only the outer alignment tool 114 or both.

An alternative (or an addition) to utilizing an inner alignment tool 112 could include a floating block 118 that is placed between the inner edges of a tube 78 and the interior of a carrier 76. A floating block 118 could have a dimensional height that is not greater than the interior height of a carrier 76. The shape of a floating block 118 could be comprised of straight lines; curved lines; or a combination thereof as illustrated in FIG. 20. In addition, a floating block 118 could have surfaces that are flat as illustrated in FIG. 20; surfaces that are concave; or a combination thereof. The floating block 118 can be made of any suitable material, such as any metal (e.g., aluminum, etc.), plastic, etc. and rests inside the inner edges of the tube 78 so that when the tube 78 is in place inside the carrier 76 the floating block 118 secures the tube 78 in place (see floating block 118 in FIG. 22). The floating block is optional.

Figure 22:
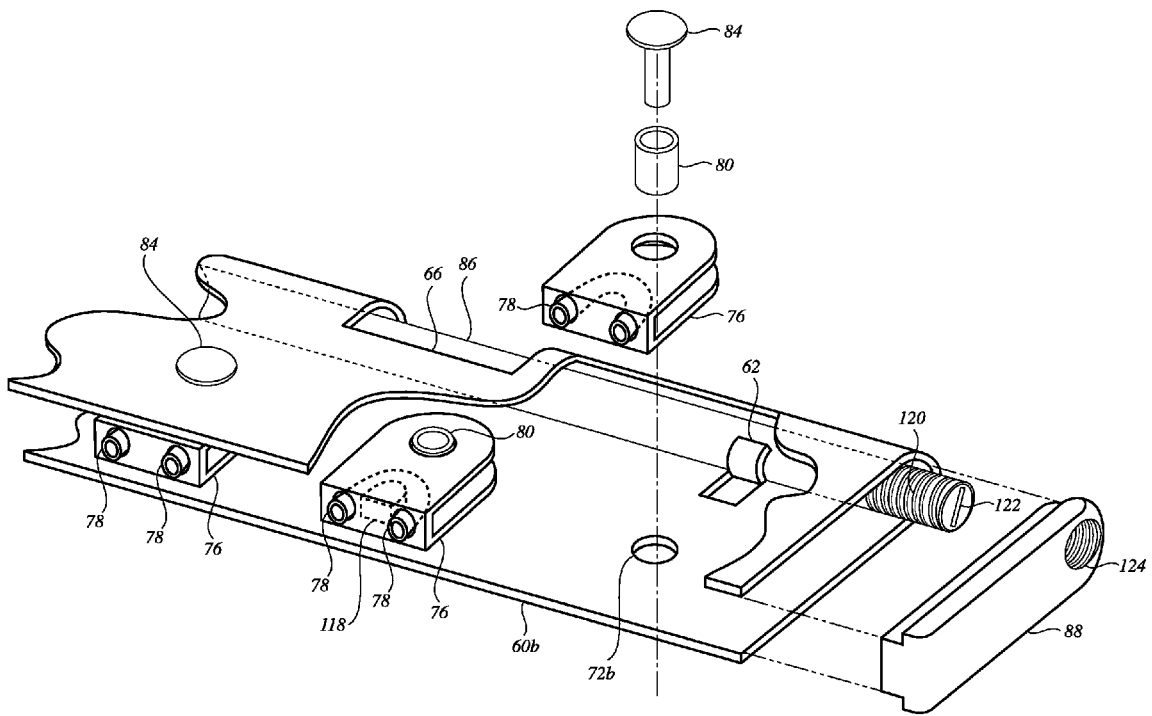
FIG. 22 is a drawing of a pulley mounting bracket with a hole in each end cap and a threaded pin, according to an embodiment.

FIG. 22 is a drawing of a pulley mounting bracket with a hole in each end cap and a threaded pin, according to an embodiment. The cut-away (missing) portion of FIG. 22 is identical (i.e. symmetrical) to the portion shown.

Figure 17:
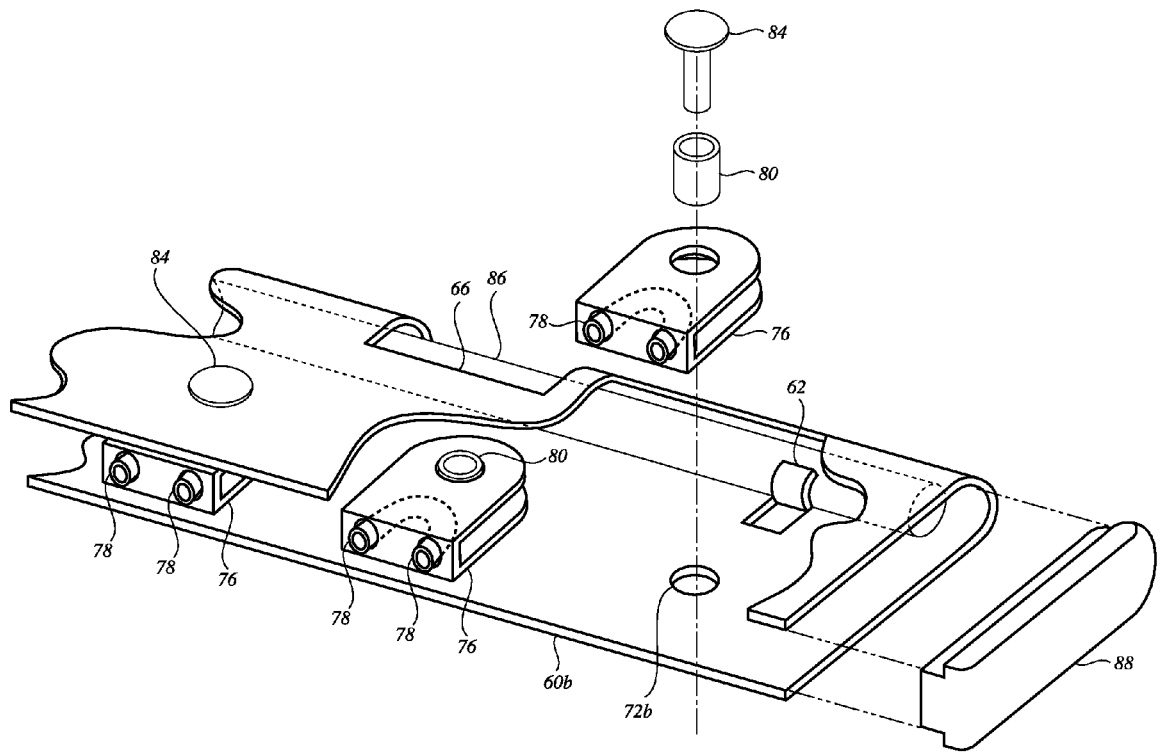
FIG. 17 is a partially exploded, partially cut-away view of the pulley mounting bracket used in the mechanical advantage closure system of FIG. 12, according to an embodiment.
Figure 18:
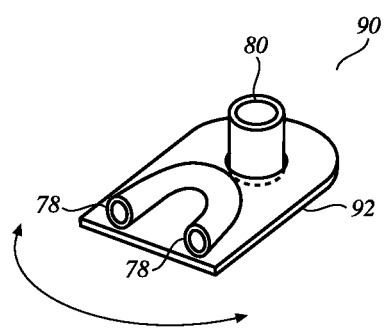
FIG. 18 is a perspective view of an alternate embodiment of a pulley assembly used in a mechanical advantage closure assembly for the orthosis device of FIG. 1, according to an embodiment.
Figure 19:
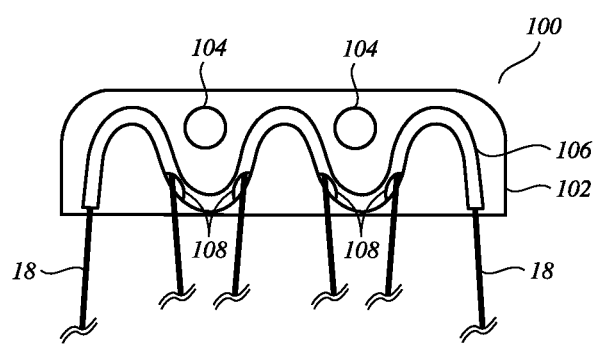
FIG. 19 is a perspective view of another alternate embodiment of a pulley assembly used in a mechanical advantage closure assembly for the orthosis device of FIG. 1, according to an embodiment.

To secure a pin 86 between two end caps 88 each end of the pin 88 can be inserted into a hole 124 built into each end cap 88. The end caps 88 (a first end cap on one side and a second end cap on the other side) could be designed with a through hole 124 that spans the entire depth; or a countersunk hole 124 that spans only a fraction of the entire depth; or no hole as illustrated in FIG. 17; or a combination thereof. Additionally, the end of the pin 86 may be smooth or threaded 120 for the purpose of creating a more secure fit with the end cap 88. An end cap 88 that receives a pin 86 with a smooth end will have a smooth cylindrical hole 124. An end cap 88 that receives a pin 86 with a threaded end 120 will have a tapped (threaded) hole 124 with compatible threads. To turn a threaded end 120 either clockwise or counterclockwise a driver head of any varying shape or size can be inserted into the corresponding recessed shape located on the drive surface 122. To further minimize movement, an end cap 88 with one or more protrusions (not illustrated) can snap, lock, or key into a mounting bracket 60a, 60b with mating slots or cutouts.

It is noted that all parts, sections, surfaces, etc., that are to be removably connected (attachable/detachable) can be done so using fasteners such as VELCRO (which uses two cooperating materials, one on each surface to be connected). "Hook fastener" and "loop fastener" as used herein refers to a fastener such as VELCRO (with cooperating material on each surface to be connected), e.g., if "loop" or "hook" fastener is used then the cooperating material is used on the other surface, and "hooks" or "loops" as used herein can be substituted with the other (with the cooperating material on the other surface to be connected).

While the above describes an orthosis device for back support, various features described herewithin may be used for other types of orthosis. For example, the mechanical advantage closure system described above may be useful for tightening other orthosis, such as knee, leg, arm, wrist, and other orthosis devices.

It should be understood, of course, that the foregoing relates to exemplary embodiments of the invention and that modifications may be made without departing from the spirit and scope of the invention as set forth in the following claims.

What is claimed is:

1. An orthotic device, comprising:
   a first side member comprising a plurality of first carriers;
   a second side member comprising comprising a plurality of second carriers;
   each of the plurality of first carriers and the plurality of second carriers comprises a top and a bottom and a front face and a hollow tube with two openings on the front face of the carrier; and
   a cord connecting the first side member and the second side member, the cord threaded through the plurality of first carriers and the plurality of second carriers through the respective hollow tubes;
   wherein at least one of the plurality of first carriers and at least one of the plurality of second carriers comprises a respective at least one opening.

2. The device as recited in claim 1, wherein the at least one opening is located at a top of the carrier.

3. The device as recited in claim 1, wherein the at least one opening is located on a side of the carrier.

4. The device as recited in claim 1, wherein the at least one opening is located on both sides of the carrier.

5. The device as recited in claim 2, wherein the at least one opening also comprises an opening located on a side of the carrier.

6. The device as recited in claim 2, wherein the at least one opening also comprises an opening on each side of the carrier.

7. The device as recited in claim 2, further comprising an inner alignment tool shaped to fit through the opening at the top of the carrier.

8. The device as recited in claim 3, further comprising an outer alignment tool shaped to fit through the opening on the side of the carrier.

9. An orthotic device, comprising:
a first side member comprising a plurality of first carriers;
a second side member comprising a plurality of second carriers;
each of the plurality of first carriers and the plurality of second carriers comprises a top and a bottom and a front face and a hollow channel with two openings on the front face of the carrier;
a cord connecting the first side member and the second side member, the cord threaded through the plurality of first carriers and the plurality of second carriers through respective channels; and
an inner alignment tool shaped to fit through the opening at the top of the carrier,
wherein at least one of the plurality of first carriers and at least one of the plurality of second carriers comprises a respective at least one opening located at a top of the carrier,
wherein the inner alignment tool comprises at least one concave notch.

10. An orthotic device, comprising:
a first side member comprising a plurality of first carriers;
a second side member comprising a plurality of second carriers;
each of the plurality of first carriers and the plurality of second carriers comprises a top and a bottom and a front face and a hollow channel with two openings on the front face of the carrier;
a cord connecting the first side member and the second side member, the cord threaded through the plurality of first carriers and the plurality of second carriers through respective channels; and
an outer alignment tool shaped to fit through the opening on the side of the carrier,
wherein at least one of the plurality of first carriers and at least one of the plurality of second carriers comprises a respective at least one opening located on a side of the carrier,
wherein the outer alignment tool comprises a concave notch.

11. An orthotic device, comprising:
a first side member comprising a plurality of first carriers;
a second side member comprising a plurality of second carriers;
each of the plurality of first carriers and the plurality of second carriers comprises a top and a bottom and a front face and a hollow channel with two openings on the front face of the carrier;
a cord connecting the first side member and the second side member, the cord threaded through the plurality of first carriers and the plurality of second carriers through respective channels; and
a tube positioned inside each channel in each of the plurality of first carriers and second carriers,
wherein at least one of the plurality of first carriers and at least one of the plurality of second carriers comprises a respective at least one opening.

12. The device as recited in claim 1, wherein a second end of the first side member is configured to attach to a second end of the second side member.

13. The device as recited in claim 1, wherein each of the plurality of first carriers and the plurality of second carriers is configured to independently swivel.

14. An orthotic device, comprising:
a first side member comprising a plurality of first carriers;
a second side member comprising a plurality of second carriers;
each of the plurality of first carriers and the plurality of second carriers comprises a top and a bottom and a front face and a hollow channel with two openings on the front face of the carrier;
a cord connecting the first side member and the second side member, the cord threaded through the plurality of first carriers and the plurality of second carriers through respective channels; and
a tube positioned inside each channel in at least one of the first carriers; and a floating block positioned between the tube.

15. An orthotic device, comprising:
a first side member comprising a plurality of first carriers;
a second side member comprising a plurality of second carriers; each of the plurality of first carriers and the plurality of second carriers comprises a top and a bottom and a front face and a hollow channel with two openings on the front face of the carrier; and
a cord connecting the first side member and the second side member, the cord threaded through the plurality of first carriers and the plurality of second carriers through respective channels,
wherein the first side member comprises an end cap that fits over a first side of the first side member and an end cap that fits over a second side of the first side member, the first side opposite the second side on the first side member.

16. The device as recited in claim 15, wherein the end cap on the first side of the first side member comprises a hole.

17. The device as recited in claim 16, wherein the end cap on the second side of the first side member comprises a hole.

18. An orthotic device, comprising:
a first side member comprising a plurality of first carriers;
a second side member comprising a plurality of second carriers;
each of the plurality of first carriers and the plurality of second carriers comprises a top and a bottom and a front face and a hollow channel with two openings on the front face of the carrier;
a cord connecting the first side member and the second side member, the cord threaded through the plurality of first carriers and the plurality of second carriers through respective channels;
an end cap on a first side of the first side member and an end cap on a second side of the first side member,
wherein the end cap on the first side of the first side member comprises a hole,
wherein the end ca on the second side of the first side member comprises a hole; and
a pin between the hole on the first side of the first side member and the hole on the second side of the first side member.

19. The device as recited in claim 18, wherein a first end of the pin is threaded and the hole on the first side of the first side member is threaded to receive the first end of the pin.

20. The device as recited in claim 19, wherein a second end of the pin is threaded and the hole on the second side of the first side member is threaded to receive the second end of the pin.

21. An orthotic device, comprising:
   a first side member comprising a plurality of first carriers;
   a second side member comprising a plurality of second carriers;
   each of the plurality of first carriers and the plurality of second carriers comprises a top and a bottom and a front face and a hollow channel with two openings on the front face of the carrier;
   a cord connecting the first side member and the second side member, the cord threaded through the plurality of first carriers and the plurality of second carriers through respective channels;
   an end cap on a first side of the first side member and an end cap on a second side of the first side member; and
   a pin which is shorter in length than a distance between the end cap on the first side of the first side member and the end cap on the second side of the first side member.

22. An orthotic device, comprising:
   a first side member comprising a first end and a second end, the first side member comprising a plurality of first carriers;
   a second side member comprising a first end and a second end, the second side member comprising a plurality of second carriers; each of the plurality of first carriers and the plurality of second carriers comprises a top and a bottom and a front face and a hollow channel with two openings on the front face of the carrier;
   a cord connecting the first side member and the second side member, the cord threaded through the plurality of first carriers and the plurality of second carriers through respective channels; and
   a pin which is longer in length than a distance between the end cap on the first end of the first side member and the end cap on the second end of the first side member,
   wherein the first side member comprises an end cap on a first end of the first side member and an end cap on a second end of the first side member.

* * * * *